(12) United States Patent
Hermet et al.

(10) Patent No.: US 8,507,237 B2
(45) Date of Patent: Aug. 13, 2013

(54) DEVICE AND METHOD FOR CONCENTRATING AND DETECTING PATHOGENIC MICROBES FROM BLOOD PRODUCTS AND/OR THEIR DERIVATIVES

(75) Inventors: Jean-Pierre Hermet, Boulogne (FR); Isabelle Besson-Faure, Aubagne (FR); Sébastien Ribault, Plan de Cuques (FR); Yann Godfrin, Lyons (FR); Anne Monnot des Angles, Saint-Remy (FR)

(73) Assignee: GeneOhm Sciences, Inc., San Diego, CA (US)

(*) Notice: Subject to any disclaimer, the term of this patent is extended or adjusted under 35 U.S.C. 154(b) by 745 days.

(21) Appl. No.: 10/795,873

(22) Filed: Mar. 8, 2004

(65) Prior Publication Data

US 2004/0185437 A1 Sep. 23, 2004

Related U.S. Application Data

(63) Continuation of application No. PCT/FR02/03132, filed on Sep. 13, 2002.

(30) Foreign Application Priority Data

Sep. 13, 2002 (FR) .................................. 01 11873

(51) Int. Cl.
- *C12N 13/00* (2006.01)
- *C12M 3/00* (2006.01)
- *G01N 33/554* (2006.01)
- *G01N 33/569* (2006.01)

(52) U.S. Cl.
USPC ............... 435/173.9; 435/2; 435/4; 435/6.15; 435/7.24; 435/7.25; 435/7.32; 435/29; 435/30; 435/39; 435/173.4; 435/176; 435/286.7; 435/287.1; 435/287.2; 435/288.5

(58) Field of Classification Search
USPC ............... 435/2, 4, 7.1, 7.2, 7.24, 7.25, 7.32, 435/13, 30, 32, 173.4, 173.9, 287.1, 287.2; 436/512, 513, 520, 521, 522, 536, 177
See application file for complete search history.

(56) References Cited

U.S. PATENT DOCUMENTS

| | | | | |
|---|---|---|---|---|
| 3,635,798 A | * | 1/1972 | Kirkham et al. | 435/2 |
| 4,435,505 A | * | 3/1984 | Zierdt | 435/2 |

(Continued)

FOREIGN PATENT DOCUMENTS

| | | |
|---|---|---|
| DE | 198 01 090 A1 | 7/1999 |
| JP | 59-192084 | 10/1984 |

(Continued)

OTHER PUBLICATIONS

Zierdt et al., (J. of Clinical Microbio. 1982. vol. 15(1):74-77).*

(Continued)

*Primary Examiner* — Ja'Na Hines
(74) *Attorney, Agent, or Firm* — Knobbe, Martens, Olson & Bear, LLP

(57) ABSTRACT

The invention concerns a device and a method for concentrating pathogenic germs potentially present in blood products or derivatives and for detecting said germs comprising the following steps: (a) subjecting a sample of said blood product to a blood cell aggregating treatment, (b) eliminating the aggregates formed at step (a) by passing the treated sample over a first filter allowing through the contaminating germs but not the cell aggregates, (c) selectively lyzing the residual cells of the filtrate obtained at step (b), (d) recuperating the contaminating germs by passing the lysate of step (c) over a second filter to detect the contaminating germs possibly trapped.

23 Claims, 12 Drawing Sheets

(56) References Cited

U.S. PATENT DOCUMENTS

| | | | |
|---|---|---|---|
| 4,727,660 A * | 3/1988 | Bernhard | 36/88 |
| 4,933,092 A * | 6/1990 | Aunet et al. | 210/729 |
| 5,302,512 A | 4/1994 | Pernelle | |
| 5,316,731 A * | 5/1994 | Schrenk et al. | 422/101 |
| 5,652,148 A | 7/1997 | Doshi et al. | |
| 5,766,552 A * | 6/1998 | Doshi et al. | 422/101 |
| 5,798,215 A * | 8/1998 | Cathey et al. | 435/7.9 |
| 5,798,221 A | 8/1998 | Egidius | |
| 5,981,294 A * | 11/1999 | Blatt et al. | 436/178 |
| 6,168,925 B1 * | 1/2001 | Besson-Faure et al. | 435/7.1 |
| 2004/0185437 A1 | 9/2004 | Hermet et al. | |
| 2006/0134729 A1 | 6/2006 | Besson-Faure et al. | |
| 2007/0202536 A1 | 8/2007 | Yamanishi et al. | |
| 2008/0145845 A1 | 6/2008 | Remacle et al. | |

FOREIGN PATENT DOCUMENTS

| | | |
|---|---|---|
| JP | 2004-000200 | 1/2004 |
| WO | WO 89/04372 | 5/1989 |
| WO | 98/22618 | 5/1998 |
| WO | WO 98/22618 | 5/1998 |
| WO | WO 01/09370 | 2/2001 |
| WO | WO 01/09370 A2 | 2/2001 |
| WO | WO 03/025207 | 3/2003 |
| WO | WO 03/085109 | 10/2003 |

OTHER PUBLICATIONS

N. Parthuisot, et al., "Evaluation of ChemChrome V6 for bacterial viability assessment in waters", Journal of Applied Microbiology 2000, 89, pp. 370-380.

Dominique Marie et al., "Application of the Novel Nucleic Acid Dyes YOYO-1, YO-PRO-1, PicoGreen for Flow Cytometric Analysis of Marine Prokaryotes", Applied and Environmental Microbiology, Washington, D.C., US, vol. 62, No. 5, May 1996 pp. 1649-1655.

R. Kepner et al., "Use of Fluorochromes for Direct Enumeration of Total Bacteria in Environmental Samples: Past and Present", Microbiological Reviews, American Society for Microbiology, Washington, D.C., U.S., vol. 58, No. 4, Dec. 1, 1994, pp. 603-615.

Weinbauer MG et al. (Dec. 1998), "Utility of green fluorescent nucleic acid dyes and aluminum oxide membrane filters for rapid Epifluorescence enumeration of soil and sediment bacteria"; Appl. Environ. Microbiol., vol. 64, No. 12, pp. 5000-5003.

Chung W et al. (2000), "Action of lysozyme and nisin mixtures against lactic acid bacteria", Int. J. Food Microbiol., vol. 60, pp. 25-32.

Hallden G. et al. (1989), "A new membrane permeabilization method for the detection of intracellular antigens by flow Cytometry", J. Immunol. Meth., vol. 124, pp. 103-109.

Helander IM et al., (2000) "Permeability barrier of the Gram-negative bacterial outer membrane with special reference to nisin.", Int. J. Food Microbiol., vol. 60, pp. 153-161.

Helander IM et al., (1997), "Polyethylenimine is an effective permeabilizer of Gram-negative bacteria", Microbiology, vol. 143, pp. 3193-3199.

Szabo Jr., G., et al. (1982) "Permeabilization of lymphocytes with polyethylene glycol 1000. Discrimination of permeabilized cells by flow cytometry", Cytometry, vol. 3, No. 1, pp. 59-63.

Plesiat, P., et al. (Nov. 1997) "Use of steroids to monitor alterations in the outer membrane of *Pseudomonas aeruginosa*", Journal of Bacteriology, vol. 179, No. 22, pp. 7004-7010.

Chung et al., "Action of lysozyme and nisin mixtures against lactic acid bacteria", International Journal of Food Microbiology 60 (2000) 25-32.

Hallden et al., "A new membrane permeabilization method for the detection of intracellular antigens by flow cytometry", J. Immunol. Meth., 1989, vol. 124, pp. 103-109.

Helander et al., "Permeability barrier of the Gram-negative bacterial outer membrane with special reference to nisin", Int. J. Food Microbiol., 2000, vol. 60, pp. 153-161.

Helander et al., "Polyethylenimine is an effective permeabilizer of Gram-negative bacteria", Microbiology, 1997, vol. 143, pp. 3193-3199.

Jacobs et al., "Evaluation of the Scansystem method for detection of bacterially contaminated platelets", Transfusion (Feb. 2005) 45(2): 265-269.

Kepner et al., "Use of fluorochromes for direct enumeration of total bacteria in environmental samples: past and present", *Microbiol. Rev.* 1994, 58(4):603.

Lew et al., "Detection of *Pseudomonas pseudomallei* by PCR and Hybridization", *J Clin Microbiol.*, (May 1994) 32(5): 1326-1332.

Makimura et al., "Detection of a wide range of medically important fungi by the polymerase chain reaction", J Med Microbiol. (1994) 40: 358-364.

Marie et al., "Application of the Novel Nucleic Acid Dyes YOYO-1, YO-PRO-1, and PicoGreen for Flow Cytometric Analysis of Marine Prokaryotes", Applied and Environmental Microbiology, May 1996, p. 1649-1655.

McDonald, "Use of a solid-phase fluorescent cytometric technique for the detection of bacteria in platelet concentrate", Transfusion Medicine (2005) 15(3): 175-183.

Parthuisot et al., "Evaluation of ChemChrome V6 for bacterial viability assessment in waters", Journal of Applied Microbiology 2000, 89, 370-380.

Plesiat et al., "Use of steroids to monitor alterations in the outer membrane of *Pseudomonas aeruginosa*", *J. Bacteriol.* 1997, 179(22):7004.

Ribault et al., "Rapid Screening Method for Detection of Bacteria in Platelet Concentrates", J Clin Microbiol (May 2004) 42(5): 1903-1908.

Ribault et al., "Detection of Bacteria in Red Blood Cell Concentrates by the Scansystem Method", J Clin Microbiol. (May 2005) 43(5): 2251-2255.

Szabo et al, "Permeabilization of lymphocytes with polyethylene glycol 1000. Discrimination of permeabilized cells by flow cytometry", Cytometry, 1982, vol. 3, No. 1, pp. 59-63.

Weinbauer et al., "Utility of Green Fluorescent Nucleic Acid Dyes and Aluminum Oxide Membrane Filters for Rapid Epifluorescence Enumeration of Soil and Sediment Bacteria", *Appl. Environ. Microbiol.* 1998, 64(12):5000.

Zierdt et al., "Lysis-filtration blood culture versus conventional blood culture in a bacteremic rabbit model", *J. Clin. Microbiol.* 1982, 15(1):74.

International Search Report mailed Jan. 3, 2003 for International Patent Application No. PCT/FR02/03132.

International Report on Patentability dated Apr. 4, 2004 for International Patent Application No. PCT/FR02/03132.

International Search Report mailed Oct. 8, 2007 for International Patent Application No. PCT/FR07/51300.

International Report on Patentability dated Dec. 10, 2008 for International Patent Application No. PCT/FR07/51300.

\* cited by examiner

DEVICE AND METHOD FOR CONCENTRATING AND DETECTING PATHOGENIC MICROBES FROM BLOOD PRODUCTS AND/OR THEIR DERIVATIVES

RELATED APPLICATION

This is a continuation of International Application No. PCT/FR02/03132, with an international filing date of Sep. 13, 2002 (WO 03/025207, published Mar. 27, 2003), which is based on French Patent Application No. 01/11873, filed Sep. 13, 2002.

FIELD OF THE INVENTION

This invention relates a method for concentrating pathogenic microbes possibly present in blood products or their derivatives as well as detecting the microbes thereby concentrated to monitor the pathogenicity of the blood products.

BACKGROUND

The term "blood product" is understood to mean whole blood as well as any preparation stemming from the fractionation of whole blood, optionally comprising cellular components. The following can be cited as examples of blood products: concentrates of red cells or platelets, but also plasma or serum preparations.

Detection of contaminations of blood products and their derivatives by different pathogenic microbes such as bacteria, viruses, molds, yeasts and others, is one of the major problems facing the public health authorities at present as well as the blood transfusion industries. Detection tests exist, but they cannot be used on a routine basis at present. The principal problems presented by most of the tests for detecting such pathogenic microbes among a population or subpopulation of blood cells are that most of the treatments that are supposed to selectively extract the pathogenic microbes simultaneously cause an elimination of these microbes. This elimination leads almost systematically to an underassessment of the presence of the microbes in the blood product tested and, thus, to an increase in the health care risk. It would therefore be advantageous to provide a new, rapid, sensitive method for detecting contamination of a blood product or its derivative by pathogenic microbes.

SUMMARY OF THE INVENTION

This invention relates to a method for detecting contaminating microbes possibly present in a blood product including blood cells including a) subjecting a sample of the blood product to an aggregation treatment of the blood cells, b) substantially eliminating aggregates formed in step (a) by passage of the sample over a first filter allowing passage of contaminating microbes, but not cell aggregates, c) selectively lysing residual cells of the filtrate obtained in step (b), d) recovering the contaminating microbes by passage of the lysate from step (c) over a second filter allowing passage of cellular debris, e) adding a marker agent of the contaminating microbes either during step (a) or step (c), and f) analyzing material on the second filter to detect labeled contaminating microbes possibly retained by the second filter.

This invention also relates to a device for concentrating contaminating microbes possibly present in a blood product including blood cells including a first watertight, sterile tank containing at least one blood cell aggregation agent and, optionally, at least one agent for labeling pathogenic microbes, a second watertight, sterile tank containing at least one lysis agent for blood cells and, optionally, at least one agent for labeling pathogenic microbes, a first filter located between the first and second tanks and capable of retaining aggregates formed in the first tank, a second filter located downstream of the second tank and capable of retaining possible contaminating pathogenic microbes, and watertight, sterile connectors placed between the first tank and the first filter, between the first filter and the second tank, and between the second tank and the second filter.

BRIEF DESCRIPTION OF THE DRAWINGS

Other advantages and characteristics of the invention will become apparent from the examples below and the attached figures in which.

DETAILED DESCRIPTION

Figure 1:
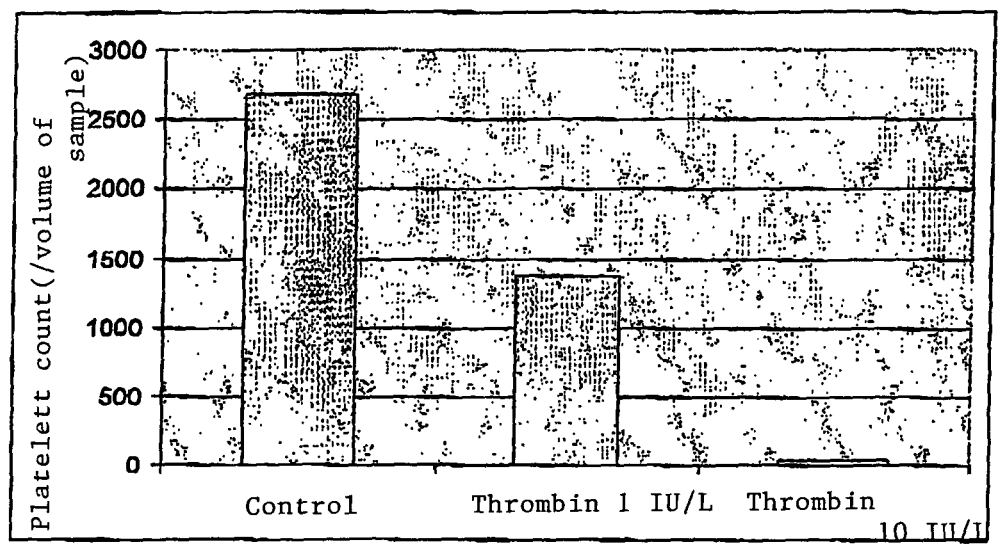
FIG. 1 is a graph illustrating platelet counting after having brought platelet concentrates into contact with different concentrations of thrombin.

The method according to aspects of the invention is remarkable in that it is performed directly on a sample stemming from a blood product collected from a subject without prior treatment or dilution. The method for detecting pathogenic microbes comprises selectively concentrating the pathogenic microbes, then, once they have been concentrated, detecting them by techniques known in the art. Selective concentration of the pathogenic microbes is performed by sequential or simultaneous elimination of the different populations of blood cells present in a blood product sample.

The method for concentrating pathogenic microbes according to aspects of the invention comprises a first step of concentrating the pathogenic microbes consisting of reducing the blood cell populations by selective aggregation of the cells, followed by a filtration step to collect in the filtrate the unaggregated, concentrated pathogenic microbes and retain on the filter the blood cell aggregates.

The term "aggregation", in the context of this invention, is understood to mean any action leading to the formation of cell aggregates. The term "cell aggregates" is understood to mean any group of cells comprising more than two cells and the size of which is greater than that of an isolated cell. In the context of this invention, an aggregate can be obtained either by aggregation, such as aggregation of platelets subsequent to their activation, an agglutination, such as agglutination of red cells obtained when they are in the presence of particular molecules, or bringing together cells induced by a change in the electrostatic charge of their membranes or other adhesion mechanisms or bringing together cells leading to the grouping together of more than two cells.

According to preferred embodiments, the aggregation of different populations of blood cells can be performed by compounds inducing platelet aggregation or compounds inducing specific agglutination of red cells. It is known, for example, that in the presence of certain compounds, the platelets have the capacity to aggregate with each other. These aggregates can be easily separated from the pathogenic microbes by filtration. The red cells also have several agglutination properties.

The method for concentrating pathogenic microbes according to aspects of the invention optionally comprises a second step of reducing the concentration of populations of the predominant cells in the blood, i.e., the platelets and the red cells, consisting of lysing the unaggregated cells isolated in the first aggregation step.

This second step of reducing the concentration of blood cell populations enables a reduction on the order of 4 log (from about $10^9$ to about $10^5$ cells/ml) regarding the concentration of platelets and on the order of 5 log (from about $10^{10}$ to about $10^5$) regarding the concentration of red cells.

More precisely, this invention provides a method for concentrating contaminating microbes possibly present in a blood product comprising blood cells, comprising the following steps:

a) a sample of the blood product is subjected to an aggregation treatment of the blood cells, b) aggregates formed in step (a) are eliminated by passage of the treated sample over a first filter allowing passage of the contaminating microbes, but not the cell aggregates, c) residual cells of the filtrate obtained in step (b) are lysed selectively, d) contaminating microbes are recovered by passage of the lysate from step (c) over a second filter allowing passage of the cellular debris.

According to a preferred embodiment, the method comprises a supplementary step of analysis of the second filter to detect the contaminating microbes possibly retained on it. The method advantageously comprises the addition of a marker agent of the contaminating microbes either during the aggregation of step (a), or during the lysis of step (c), or directly on the second filter during the analysis step (e).

A marker solution comprising an esterase substrate such as ChemChrome V6 is an example of a marker agent of the pathogenic microbes detectable by the method of this invention. Thus, it is possible to use a marker solution comprising a labeled antibody or a marker of nucleic acids. The marker is preferably fluorescent or coupled to a fluorochrome or an enzyme enabling degradation of a substrate thereby made fluorescent, with the possibility that the fluorescence can be detected by an excitation laser.

The method also comprises addition of a permeabilization agent of the contaminating microbes which can be added to at least one of the steps, either during the aggregation of step (a), or during the lysis of step (c), or directly on the second filter during the analysis of step (e), or during several of these steps.

Examples of permeabilization agents of the contaminating microbes include, but are not limited to, polyethylene imine, chlorhexidine diacetate, chlorhexidine digluconate, ethylene diamine tetraacetate acid (EDTA) alone or in combination with nisin as well as detergents such as N-octyl β-D-glucopyranoside, SDS, Tween, triton, Brij and the like.

According to a preferred embodiment, the blood cells of the blood product are platelets or red cells or a mixture of these two. According to another preferred embodiment, the blood cells of the blood product are platelets and the aggregation treatment of step (a) comprises bringing the sample into contact with an aggregation composition comprising at least one of the aggregation agents selected from the group comprising: 1) a specific antibody of a platelet antigen, 2) a strong agonist of platelet activation selected from among: thrombin, TRAP (thrombin receptor activating peptide), trypsin, collagen, thromboxane A2 or ionophore A23187, and 3) a weak agonist of platelet aggregation selected from among ADP, adrenalin, arachidonic acid, Von Willebrand factor, serotonin or epinephrine.

The concentration of CD9 antibody specific of a platelet antigen in the aggregation composition is advantageously between about 0.5 μg/ml and about 100 μg/ml, preferably between about 5 μg/ml and about 40 μg/ml.

The concentration of strong agonist in the aggregation composition is advantageously between:

about 0.5 IU/ml and about 100 IU/ml, preferably between about 1 IU/ml and about 20 IU/ml, for a thrombin type agonist;

about 5 μM and about 200 μM, preferably between about 10 and about 100 μM, for a TRAP type agonist;

about 1 nM and about 500 nM, preferably between about 10 nM and about 300 nM, for a trypsin type agonist;

about 0.05 μg/ml and about 50 μg/ml, preferably between about 1 μg/ml and about 20 μg/ml, for a collagen type agonist;

about 0.01 μg/ml and about 5 μg/ml, preferably between about 0.1 and about 1 μg/ml, for a thromboxane A2 type agonist;

about 0.005 mg/ml and about 1 mg/ml, preferably between about 0.05 and about 0.5 mg/ml, for a PAF type agonist;

about 0.1 μM and about 100 μM, preferably between about 1 μM and about 20 μM, for an ionophore A23187 type agonist.

The concentration of weak agonist in the aggregation composition is advantageously between:

about 0.5 μM and about 100 μM, preferably between about 1 μM and about 20 μM, for an agonist of the ADP, adrenalin or epinephrine type;

about 0.001 mM and about 10 mM, preferably between about 0.01 mM and about 5 mM, for an agonist of the arachidonic acid type;

about 0.001 mg/ml and about 1 mg/ml, preferably between about 0.01 mg/ml and about 0.5 mg/ml, for an agonist of the Von Willebrand factor type;

about 0.05 μand about 100 μM, preferably between about 0.01 μM and about 50 μM, for an agonist of the serotonin type.

The specific antibody of a platelet antigen is preferably selected from among: an anti-CD, CD32, anti-PTA1, CD42, anti-GpIIb/IIIa and anti-GpIV antibody.

According to another embodiment, the blood product comprises red cells and the aggregation treatment of step (a) comprises bringing the sample into contact with an agglutination composition comprising at least one agglutination agent selected from among the lectins, polyethylene imine, polyvinylpyrrolidone (PVP), gelatins, dextrans or polyethylene glycols (PEG). The lectins advantageously have an erythroagglutinin activity. Most preferably, the lectins are selected from among the lectins of *Phaseolus vulgaris, Vicia sativa, Vicia faba* or *Erythrina corallodendron, Lens culinaris, Phytolacca Americana* or *Triticum vulgaris*. The concentration of *Phaseolus vulgaris* type lectin in the agglutination composition is advantageously between about 10 µg/ml and about 200 µg/ml.

The concentration of polyethylene imine in the agglutination composition is advan-tageously between about 0.1% (weight/volume) and about 40% (weight/volume). The dextrans are most preferably selected from among Dextran 70, Dextran 100, Dextran 500 and the like. The concentration of dextran in the agglutination composition is advantageously between about 0.1% (weight/volume) and about 40% (weight/volume).

The PEG compounds are most preferably selected from among PEG35, PEG and the like. The concentration of PEG in the agglutination composition is advantageously between about 0.05% (weight/volume) and about 40% (weight/volume). The concentration of gelatin in the agglutination composition is advantageously between about 0.5% (weight/volume) and about 40% (weight/volume).

The PVP compounds are most preferentially selected from among PVP-40, PVP-360 and the like. The concentration of PVP in the agglutination composition is advantageously between about 0.05% (weight/volume) and about 40% (weight/volume).

Lysis of the cells of step (c) is advantageously performed with a lysis solution comprising one or more detergents selected from saponin, SDS TWEEN 20, TRITON X100, Brij 96, Polido-canol, N-octyl β-D-glucopyranoside and sodium carbonate. The lysis solution is preferably constituted of a mixture of saponin, TRITON X100 and TWEEN 20. Most preferably, the lysis solution comprises saponin at a concentration (expressed in weight/volume %) between about 0.005% and about 0.5%, of TRITON X100 at a concentration (expressed in weight/volume %) between about 0.001% and about 0.5% of TWEEN 20 at a concentration between about 0.01% and about 1% and of N-octyl β-D-glucopyranoside at a concentration between about 0.1% and about 0.5%.

Permeabilization of the bacteria is advantageously performed with a solution comprising one or more reagents selected from chlorhexidine (digluconate, diacetate), polyethylene imine, N-octyl β-D-glucopyranoside, nisin alone or in combination with EDTA. The permeabilization agents are preferably used in the case of chlorhexidine at a concentration (weight/volume) between about 0.0001% (weight/volume) and about 0.1% (weight volume), in the case of polyethylene imine at a concentration between about 5 µg/ml and about 120 µg/ml, in the case of N-octyl β-D-glucopyranoside at a concentration between about 0.1% (weight/volume) and about 0.5% (weight/volume) and in the case of nisin between about 0.1 µg/mL and about 0.5 µg/mL alone or in combination with EDTA at a concentration between about 1 mM and about 10 mM.

The method of the invention can be used to concentrate and detect numerous contaminating microbes of blood products such as aerobic and anaerobic bacteria, molds, yeasts, live and/or dead bacterial spores. The size of the pores of the first filter is advantageously between about 2 µm and about 20 µm. The size of the pores of the second filter is advantageously between about 0.2 µm and about 2 µm.

Detection of the contaminating microbes of step (e) of the method of the invention is advantageously performed in an enclosed device. Most preferably, the contaminating microbes capable of being concentrated are selected from among the groups of aerobic and anaerobic bacteria, molds, yeasts and live and/or dead bacterial spores. The size of the pores of the first filter is between about 2 µm and about 20 µm, and the size of the pores of the second filter is between about 0.2 µm and about 2 µm.

Figure 12:
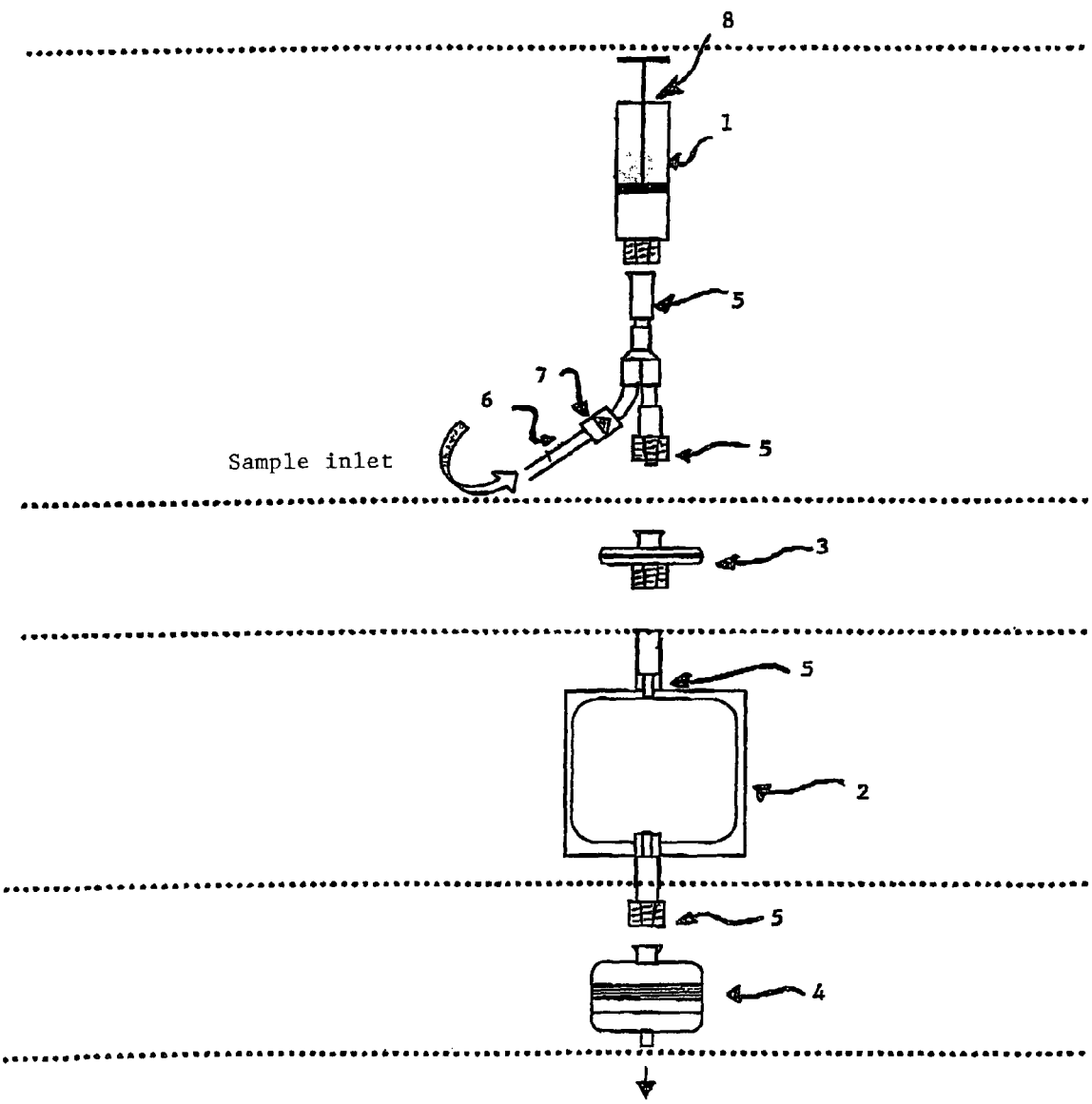
FIG. 12 is a schematic perspective view illustrating a preferred embodiment of the device for concentrating pathogenic microbes according to aspects of the invention.

This invention also provides a device for concentrating and labeling contaminating microbes possibly present in a blood product comprising, as shown in FIG. 12:

a first watertight, sterile tank (1) containing at least one blood cell aggregation agent and possibly at least one agent for labeling pathogenic microbes;

a second watertight, sterile tank (2) containing at least one lysis agent for blood cells and possibly at least one agent for labeling pathogenic microbes;

a first filter (3) placed between the first and second tanks and capable of retaining the aggregates formed in the first tank;

a second filter (4) placed downstream of the second tank and capable of retaining the possible contaminating pathogenic microbes; and watertight, sterile connector (5) placed between the first tank (1) and the first filter (3), between the first filter (3) and the second tank (2), and between the second tank (2) and the second filter (4).

According to a preferred embodiment, the device comprises a watertight, sterile connector (6) to connect the bag containing the blood product to the first sterile tank (1). The watertight, sterile connection (6) connecting the bag containing the blood product to the first sterile tank is advantageously equipped with a reverse lock valve (7).

According to another preferred embodiment, the device comprises a sampling device to sample a determined volume of the blood product directly from a storage bag of the product into the first tank (1).

The first watertight, sterile tank (1) is advantageously fitted with a sample suctioning system (8). The suctioning system is preferably a piston. According to another preferred embodiment, the second filter (4) is enclosed in a membrane support composed of two parts that can be separated for removing the filter. The device i advantageously enclosed and sterile.

EXAMPLES

I. Concentration of Pathogenic Microbes by an Aggregation Step

I.1 Aggregation of Platelets

Example 1

Aggregation with a Strong Agonist: Thrombin

Thrombin is a strong agonist of platelet aggregation. Thrombin solutions (reference T8885 Sigma) were prepared at a concentration of 100 IU/ml when used at the rate of 10 IU/test and in diluted solution form (100 µl of thrombin mother solution with the addition of 900 µl of PBS buffer) when used at the rate of 1 IU/test.

Platelet aggregation by the intermediary of thrombin comprised:

placing 160 µl of platelet concentrate in a tube to which was added 20 µl of PBS buffer and 20 µl of thrombin;

the tubes were agitated manually for 5 minutes at ambient temperature;

800 µl of PBS buffer was added to the tubes;
the content of the tubes was filtered on a filter with a porosity of 11 µm;
dilutions were created in series 1/20 to 1/10 from the filtrates;
100 ml of each dilution of the filtrate on a CB04 membrane were filtered;
an esterase labeling was performed; and
the platelets possibly retained on the membrane were counted.

Table 1 below illustrates the results obtained and shows the number of platelet aggregates obtained in the presence of thrombin used at two different concentrations. FIG. 1 graphically illustrates these results.

TABLE 1

|      | Control | 1 IU thrombin | 10 IU thrombin |
|------|---------|---------------|----------------|
| PC 6 | 1584    | 374           |                |
|      | 1535    | 490           |                |
| PC 6 | 2622    | 1358          | 44             |
|      | 2737    | 1399          | 30             |

Example 2

Platelet Aggregation with Thrombin in the Presence of Pathogenic Microbes

The experimental studies performed to evaluate the aggregation of pathogenic microbes in the presence of thrombin comprised the following steps:
a cryobead of *E. coli* was introduced into a tube of 9 ml of tryptone soy broth and incubated at 37° C. for 18-24 hours;
160 µl of platelet concentrate was added to 20 µl of the *E. coli* suspension and 20 µl of thrombin;
the tube was agitated manually for 5 minutes at ambient temperature;
800 µl of PBS buffer was added;
filtration was performed through a filter of 11 µm porosity;
dilutions in series were performed: 1/20 and 1/10 and 1/10;
filtration was performed on 100 µl of sample on a CB04 membrane;
labeling with esterase was performed; and
detection was performed.

Table 2 below shows the aggregation of the platelet concentrates with thrombin in the presence of *E. coli*.

TABLE 2

| Pathogenic microbe | Platelet preparation | Thrombin | Counting results |
|--------------------|----------------------|----------|------------------|
| *E. coli*          | —                    | —        | 1921             |
|                    | —                    | —        | 1999             |
| *E. coli*          | PC 6                 | —        | 657              |
|                    |                      |          | 763              |
| *E. coli*          | PC 6                 | 1 IU     | 140              |
|                    |                      |          | 167              |
| *E. coli*          | PC 6                 | 10 IU    | 109              |
|                    |                      |          | 122              |

A clot appeared almost instantly after addition of the thrombin.

Example 3

Platelet Aggregation in the Presence of a Weak Agonist: ADP

ADP (Sigma) was used at a concentration of 200 µM in distilled water.

The experimental studies performed to evaluate platelet aggregation in the presence of ADP comprised the following steps:
400 µl of platelet concentrate was introduced into a tube to which was added 50 µl of PBS buffer and 50 µl of ADP;
the tubes were agitated manually for 5 minutes at ambient temperature;
500 µl of PBS buffer was added;
dilutions were performed in series of 1/20 and 1/10 and 1/10;
100 µl of sample was filtered on a CB04 membrane;
labeling with esterase was performed; and
detection was performed.

The results illustrated in FIG. 1 show that, in the presence of ADP, the concentration of platelets was reduced by about 50% to about 90%.

Example 4

Platelet Aggregation with ADP in the Presence of Pathogenic Microbes

Platelet aggregation in the presence of ADP comprised the following steps:
a cryobead of *Staphylococcus epidermidis* was introduced into a tube of 9 ml of tryptone soy broth and incubated at 37° C. for 18-24 hours;
onto 400 µl of platelet concentrate there was added 50 µl of the suspension of *Staph. epidermidis* and 50 µl of ADP;
the tubes were agitated manually for 5 minutes at ambient temperature;
500 µl of PBS buffer was added;
filtration was performed on a filter with a porosity of 5 µm;
dilutions were made in series of 1/20 and 1/10 and 1/10;
100 µl of the sample was filtered on a CB04 membrane;
labeling with an esterase was performed; and
detection was performed.

The pathogenic microbes were seeded at a high concentration to augment a possible trapping effect. ADP was added to the platelets and the bacteria at a concentration of 10 µM.

TABLE 3

| Pathogenic microbe | Platelet preparation | Aggregation agent | Results | Concentration bacteria/ml |
|--------------------|----------------------|-------------------|---------|---------------------------|
| *Staphylococcus epidermidis* | PC 6 | none | 590 | 6.0E+07 |
|                    |                      |                   | 605     |                           |
| *Staphylococcus epidermidis* | PC 6 | 10 µM ADP | 492 | 4.7E+07 |
|                    |                      |                   | 441     |                           |

The results obtained, shown in Table 3 above, show that 74% of bacteria are recovered after the aggregation step.

Example 5a.

Platelet Aggregation in the Presence of a CD9 Antibody

It is known that the CD9 antibody induces platelet activation and, consequently, their aggregation. Tests were performed with two CD9 clones, clone SN4 (Ancel, ref. 156-020, con-centration 100 µg/ml) and clone 6B1 (Hemosystem).
The selective aggregation method implemented with these CD9 antibodies comprised the following steps:
400 µl of platelet concentrate was added to 50 µl of PBS buffer and 50 µl of CD9 antibody;

the tubes were agitated manually for 5 minutes at ambient temperature;

500 µl of PBS buffer was added;

filtration was performed on a filter with a porosity of 5 µm;

dilutions were performed in series of ⅟20 and ⅟10 and ⅟10;

100 µl of sample was filtered on a CB04 membrane;

labeling was performed with an esterase; and detection was performed.

Figure 2:
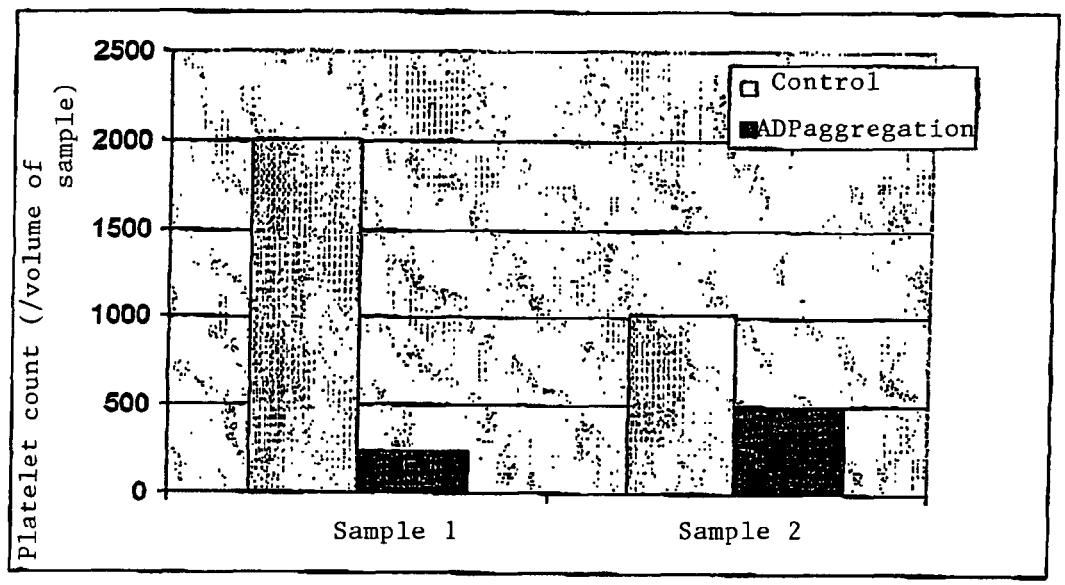
FIG. 2 is a graph illustrating platelet counting after aggregation in the presence of ADP for two platelet samples.

The CD9 antibody (clone SN4) was used in the presence of platelets at a final concen-tration of 10 µg/ml. FIG. 2 illustrates platelet aggregation obtained in the presence of antibody CD9 (clone SN4). A dose-response curve was established to evaluate the concentration of anti-body CD9 required for platelet aggregation.

Method:

400 µl of platelet concentrate placed in tubes was added to different dilutions of antibody, with final concentrations ranging from 0 to 20 µl/ml of antibody CD9;

the tubes were agitated manually for 5 minutes at ambient temperature;

500 µl of PBS buffer was added;

filtration was performed on a filter with a porosity of 5 µm;

dilutions were performed in series: four ⅟10 dilutions;

100 µl of sample was filtered on a CB04 membrane;

labeling was performed with an esterase; and detection was performed.

Figure 3:
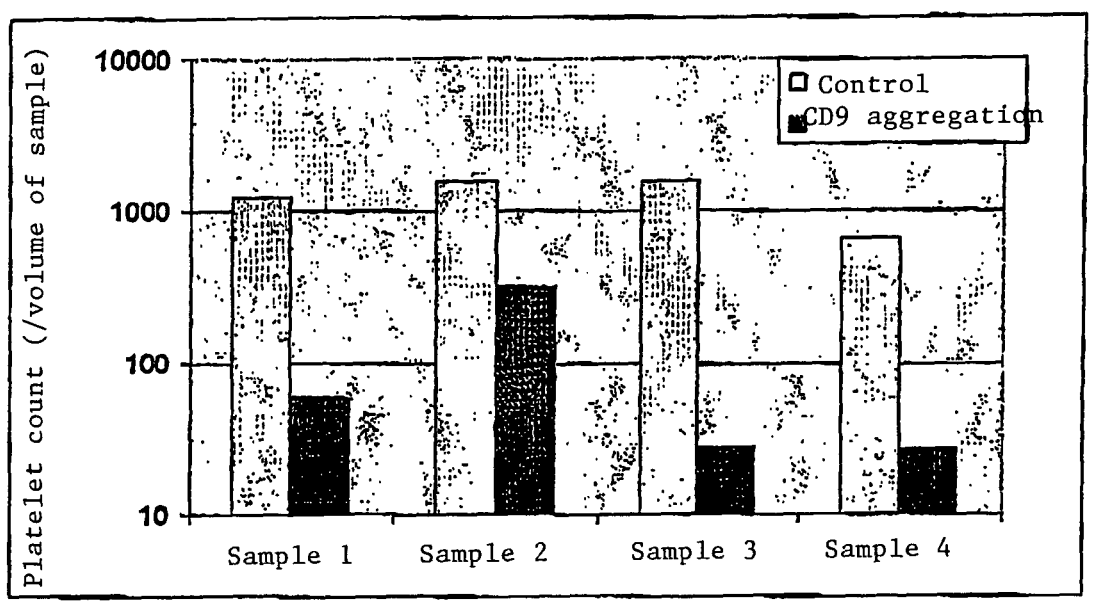
FIG. 3 is a graph showing the platelet counting in the presence of CD9 antibodies (clone SN4) for four platelet samples.
Figure 5:
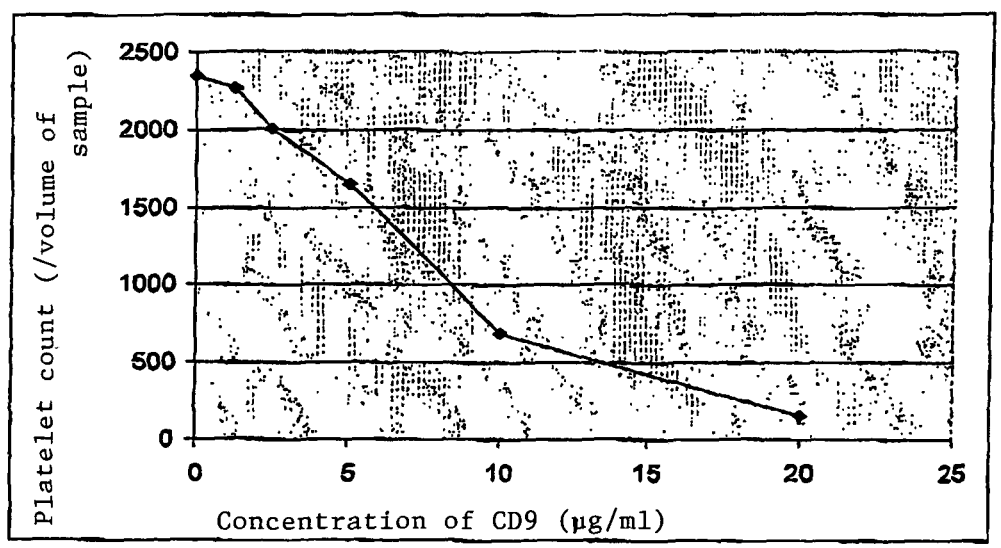
FIG. 5 is a graph showing a dose response curve obtained in the presence of increasing concentrations of antibody CD9 (clone SN4)

FIGS. 3 and 5 show, respectively, the counting results for aggregated platelets in the presence of increasing doses of antibody CD9 (clone SN4) and the dose-response curve thereby obtained. Counting of the residual platelets was performed with the analyzer.

The aggregation was dose dependent. The concentration of CD9 was increased as much as possible to increase the effect of aggregation. However, a compromise was established for detecting the bacteria. It was determined that the platelet concentration could be reduced from 1 to 2 log by using a concentration of about 10 µg/ml of antibody CD9.

Example 5b:

A dose-response curve was established to evaluate the concentration of antibody CD9 (clone 6B1) for platelet aggregation.

Method:

3 mL of platelet concentrate placed in tubes was added to different dilutions of antibody, with final concentrations ranging from 2.5 µg/mL to 40 µl/mL of antibody CD9;

the tubes were agitated manually for 15 minutes at ambient temperature;

filtration was performed on a filter with a porosity of 5 µm; and platelet counting was performed as described above.

Figure 4:
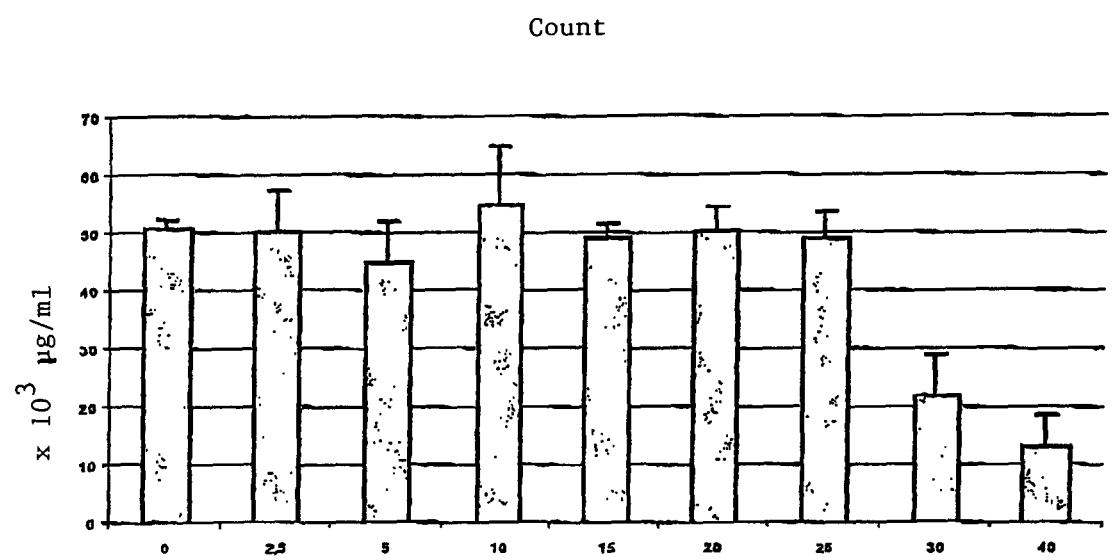
FIG. 4 is a graph showing the results of platelet counting in the presence of increasing doses of antibody CD9 (clone 6B1) used in 3 mL of platelet concentrate.

Attached FIG. 4 shows the counting results for aggregated platelets in the presence of increasing doses of antibody CD9 (clone 6B1).

Example 6

Platelet Aggregation with the CD9 Antibody in the Presence of Bacteria

Method:

a cryobead of *Staphylococcus epidermidis* was introduced into a tube of tryptone soy broth and incubated at 37° C. for 18-24 hours;

400 µl of platelet concentrate placed in tubes was added to 50 µl of the *Staphylococcus epidermidis* suspension and 50 µl of CD9;

the tubes were agitated manually for 5 minutes at ambient temperature;

500 µl of PBS buffer was added;

filtration was performed on a filter with a porosity of 5 µm;

dilutions were performed in series: four dilutions ⅟10;

filtration of 100 µl of the sample was performed on a CB04 membrane;

labeling was performed with an esterase; and detection was performed.

Table 4 below illustrates platelet aggregation with CD9 in the presence of bacteria.

TABLE 4

| Bacteria | CD9 | | Result | % recovery |
|---|---|---|---|---|
| Staph. epidermidis | PC 10 | — | 46 44 | 93 |
| Staph. epidermidis | PC 10 | +agitation | 43 48 | |
| E. coli | PC 10 | | 218 243 | 64 |
| E. coli | PC 10 | CD9 + agitation | 166 148 | |

These results show that the *Staphylococcus epidermidis* bacteria were recovered in a pronounced manner. For *E. coli*, the count was reduced by 36%.

I.2 Agglutination of Red Cells

Lectins are glycoproteins of nonimmune origin that agglutinate cells and/or precipitate carbohydrate complexes. These molecules readily bond with specific carbohydrates.

Two lectins were used: Phaseolus vulgaris PHA-E and *Vicia sativa*.

Example 1

Agglutination of Red Cells with Lectins

*Phaseolus vulgaris* PHA-E lectin (Sigma) was used at a concentration of 2 mg/ml in PBS. *Vicia sativa* lectin (Sigma) was used at the concentration of 1 mg/ml. A quick evaluation of the two lectins revealed that there is no red cell agglutination with *Vicia sativa*. On the other hand, *Phaseolus vulgaris* induced a rapid and effective agglutination.

Method:

400 µl of red cells were placed in tubes to which were added 50 µl of PBS and 50 µl of *Phaseolus vulgaris*;

the tubes were agitated manually for 5 minutes at ambient temperature;

500 µl of PBS buffer was added;

filtration was performed on a filter with a porosity of 5 µm;

dilutions were performed in series: four ⅟10 dilutions;

labeling was performed with an anti-glycophorine-PE antibody; and detection was performed.

Figure 6:
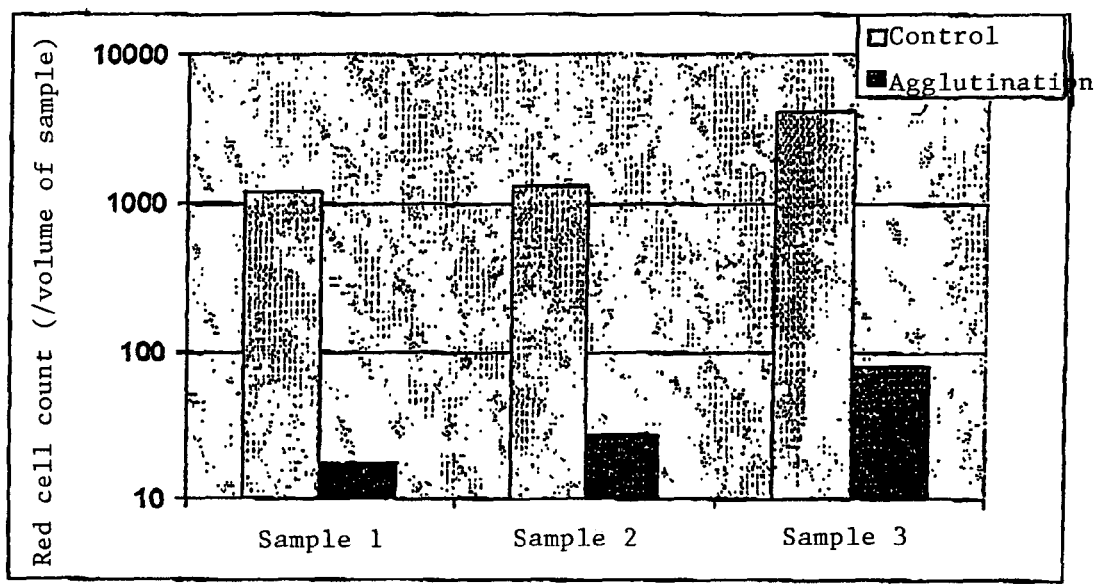
FIG. 6 is a graph illustrating the agglutination of red cells in the presence of *Phaseolus vulgaris* lectin used at a concentration of 200 µg/ml for three samples of red cell concentrates.

FIG. 6 shows agglutination of the red cells obtained in the presence of *Phaseolus vulgaris*. *Phaseolus vulgaris* was used in this test at a concentration of 200 µg/ml. We saw a reproducible decrease of two logs in the concentration of red cells in the presence of Phaseolus vulgaris.

Example 2.

Agglutination of Red Cells in the Presence of Bacteria

The preliminary tests showed that there is no interaction between the Phaseolus lectin and the bacteria.

Method:

a cryobead of E. coli was introduced into a tube of 9 ml of tryptone soy broth and incubated at 37° C. for 18-24 hours;

400 μl of PBS, 50 μl of E. coli (pure culture) and 50 μl of Phaseolus vulgaris was mixed in the tubes;

the tubes were agitated manually for 5 minutes at ambient temperature;

500 μl of PBS buffer was added;

filtration was performed on a 5-μm filter;

dilutions were performed in series: four dilutions $\frac{1}{10}$;

filtration was performed on 100 μl of the sample on a CB04 membrane;

labeling was performed with an esterase; and detection was performed.

The results obtained using a Phaseolus vulgaris concentration of 200 μg/ml are shown in Table 5 below.

TABLE 5

| Bacteria | Red Cells | Lectin (concentration) | Count | % recovery |
|---|---|---|---|---|
| E. coli NCTC 9001 | RBC 9 | | 662 604 | |
| E. coli NCTC 9001 | RBC 9 | Phaseolus 200 ug/ml | 544 579 | 91 |

These results show that 91% of the bacteria were detected after the agglutination step and that after this agglutination step, the red cell concentration was reduced by two logs while the strain E. coli was still recovered in a pronounced manner.

II. Concentration of Pathogenic Microbes by Means of a Lysis Step

We evaluated the different selective lysis techniques enabling elimination of blood cells without affecting the concentration of the bacteria possibly present in the samples to be analyzed.

Following several preliminary studies, we observed that certain bacteria were resistant in the presence of detergents such as TRITON X100 and determined the concentration of detergents with which the bacteria recovery percentage is desired.

Example 1.

Effect of the formulation of the lysis solution on pure bacterial cultures

Method:

the strains were preserved in a tube of 9 ml of tryptone soy broth and incubated at 37° C. for 18 - 24 hours;

dilutions in series ($\frac{1}{10}$) were performed in the PBS buffer up to $10^{-5}$;

one milliliter of the last dilution was treated with 9 ml of the lysis solution 0.01% (weight/volume) of saponin, 0.1% (weight/volume) of TWEEN and 0.001% (weight/volume) of TRITON X 100 for 15 minutes;

100 μl of the sample was filtered on a CB04 membrane;

labeling was performed with an esterase; and detection was performed.

The results of these different tests are illustrated in Table 6 below in which are expressed the different bacteria recovery percentages obtained.

TABLE 6

| Strain | Control | Lysed sample | % recovery |
|---|---|---|---|
| E. coli | 132 145 | 153 119 | 98 |
| Bacillus cereus | 465 572 | 61 54 | 11 |
| E. coli | 52 54 | 44 44 | 83 |
| Staph. epidermidis | 2952 3069 | 3024 3020 | 101 |
| E. aerogenes | 841 802 | 880 925 | 110 |
| Ps. aeruginosa | 261 215 | 82 66 | 31 |
| Staph. aureus | 105 94 | 126 122 | 125 |
| P. mirabilis | 729 906 | 1129 1151 | 139 |
| S. typhimurium | 608 600 | 820 787 | 133 |
| Serratia marcescens | 1848 1775 | 1826 1860 | 102 |
| C. amycolatum | 1103 1167 | 1512 2035 | 156 |
| K. pneumoniae | 72 82 | 79 73 | 99 |
| P. fluorescens | 4039 3951 | 4873 5105 | 125 |
| Streptococcus bovis | 3074 2939 | 1848 1978 | 64 |
| Y. enterocolitica | 10,218 10,321 | 9888 10,526 | 99 |

Figure 7:
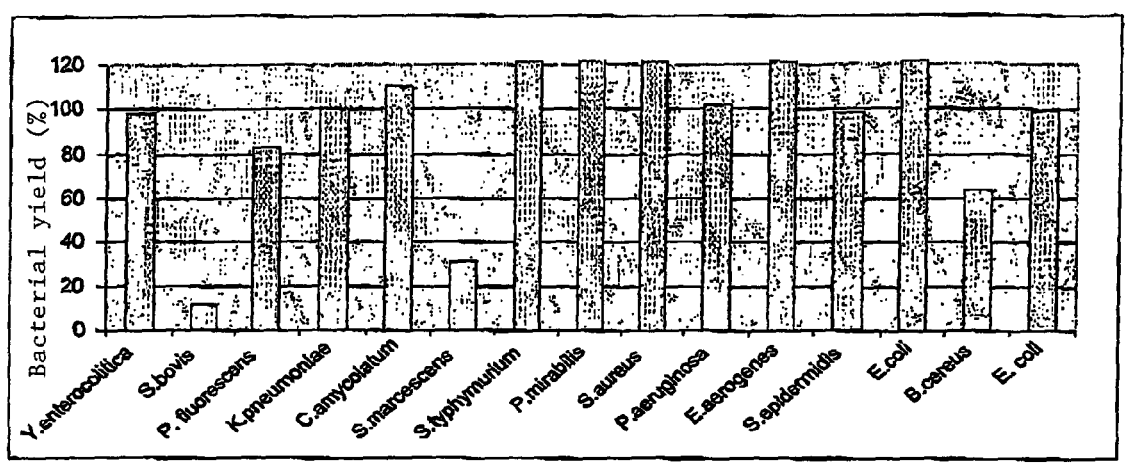
FIG. 7 is a graph showing the effects of the lysis solution on the recovery of different pathogenic microbes in pure cultures.

These results are illustrated in FIG. 7.

Most of the strain are not affected by the lysis solution. The recovery percentages are consistent predefined predictions, between 85 and 115%, except for Ps. aeruginosa and Bacillus cereus.

Example 2a

Effect of the Formulation of the Lysis Solution on the Bacteria Seeded in the Platelets Two strains were adapted to the growth in the platelet concentrates to simulate a contamination.

Method:

the strains Bacillus cereus and Staph. aureus were seeded in platelets in 50-ml tubes using a concentration of $10^6$ cells in 20 ml of platelets;

the 50-ml tubes were kept in the platelet incubator at 22° C. for several days;

one milliliter of seeded platelets was diluted with 9 ml of the lysis solution;

lysis was performed for 15 minutes at ambient temperature;

100 μl of the sample was filtered on a CB047 membrane;

the bacteria were labeled with a stearic substrate; and the membrane was scanned with the analyzer.

The bacteria count results after lysis are illustrated in Table 7 below.

TABLE 7

|  |  | Control | Lysed |
|---|---|---|---|
| Bacillus cereus | bacteria/ml | 16 | 14 |
|  |  | 24 | 27 |
|  |  | 2.0E+06 | 2.1E+06 |
| Staph. aureus | bacteria/ml | 1966 | 1885 |
|  |  | 2046 | 1901 |
|  |  | 2.0E+08 | 1.9E+08 |

The bacteria were seeded at an initial concentration of $5 \cdot 10^3$ cells/ml and detected several days later at concentrations on the order of $10^6$ to $10^9$ cells/ml. It can be seen from these experiments that the bacteria that developed in the platelets were not affected by the lysis solution.

Example 2b

Effect of the Formulation of the Lysis Solution on the Pure Bacteria Cultures

Figure 11:
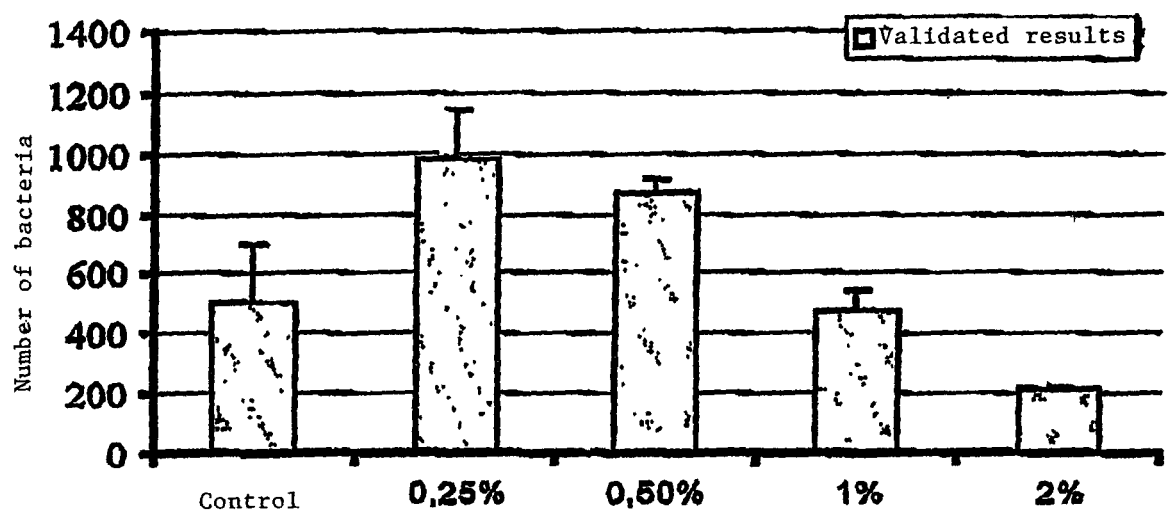
FIG. 11 is a graph illustrating the effect of the concentration of N-octyl β-D-glucopyranoside in the lysis solution on the pure bacteria cultures.

Method:
the strains were preserved in a tube of 9 ml of tryptone soy broth and incubated at 37° C. for 18-24 hours;
after determination of the number of bacteria by esterase labeling, 3000 bacteria were inoculated in 3 mL of PBS;
the 3 mL were treated with the lysis solution (NOG 0.25% to 2%) for 20 minutes;
the totality of the sample was filtered on a CB04 membrane; and
counting was performed in solid phase cytometry.
The results obtained are illustrated in FIG. 11.

Example 3

Effect of the Formulation of the Lysis Composition on the Red Cells

Figure 9:
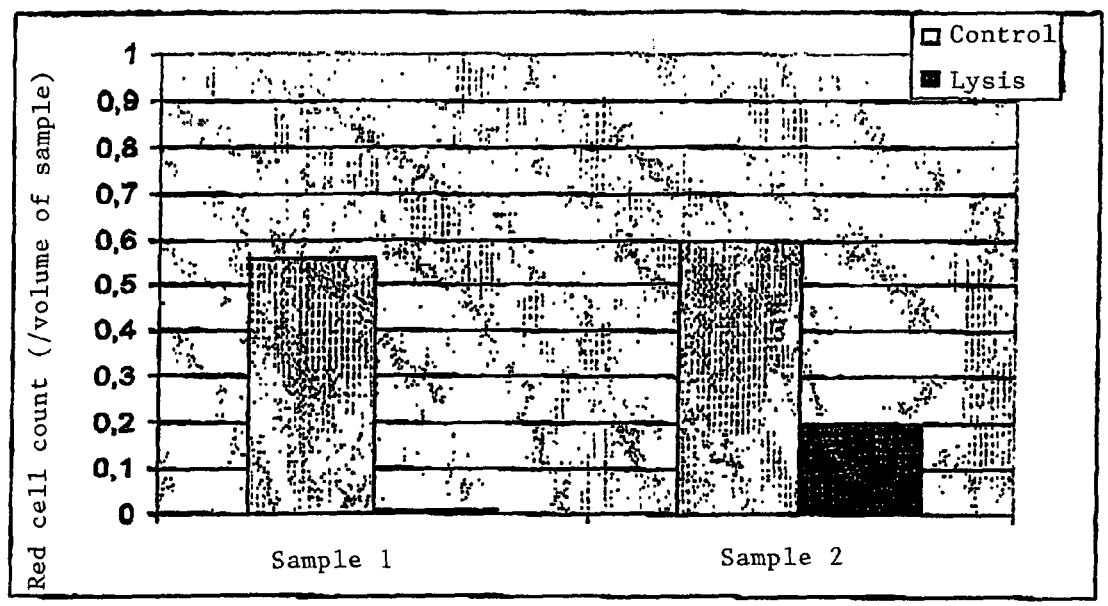
FIG. 9 is a graph illustrating the effects of lysis on the erythrocyte count of two different samples of red cell concentrate.
Figure 10:
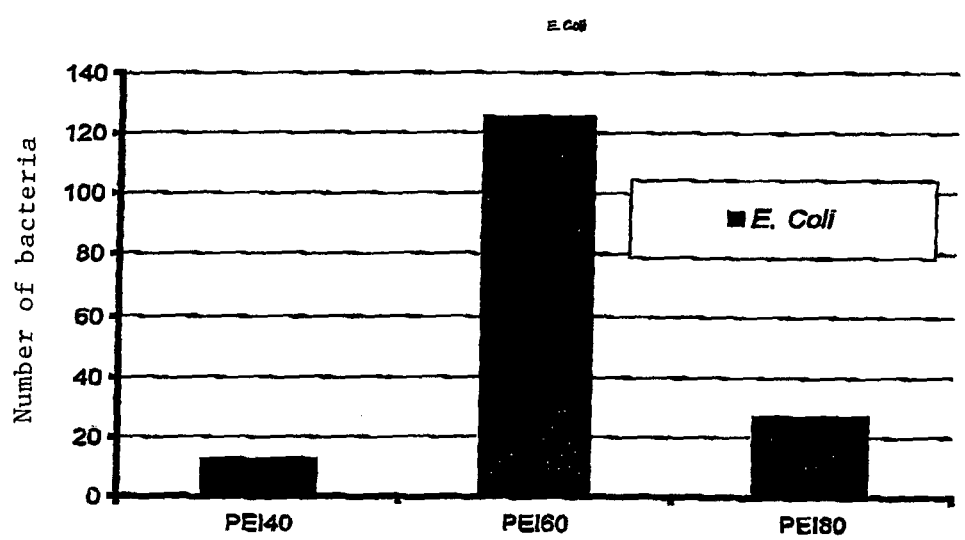
FIG. 10 is a graph illustrating the counting of *Escherichia coli* bacteria within a platelet sample using polyethylene imine (PEI) as a permeabilization agent to increase penetration of the marker.

Method:
one milliliter of red cells was diluted in 9 ml of lysis solution or 9 ml of PBS (control);
lysis was performed for 15 minutes at ambient temperature; and
the lysed or non-lysed samples were analyzed using a cell counter.
FIG. 9 shows the results obtained on the lysed red cell preparation compared to the non-lysed red-cell preparation.

Example 4

Effect of the Formulation of the Lysis Composition on the Platelets

Figure 8:
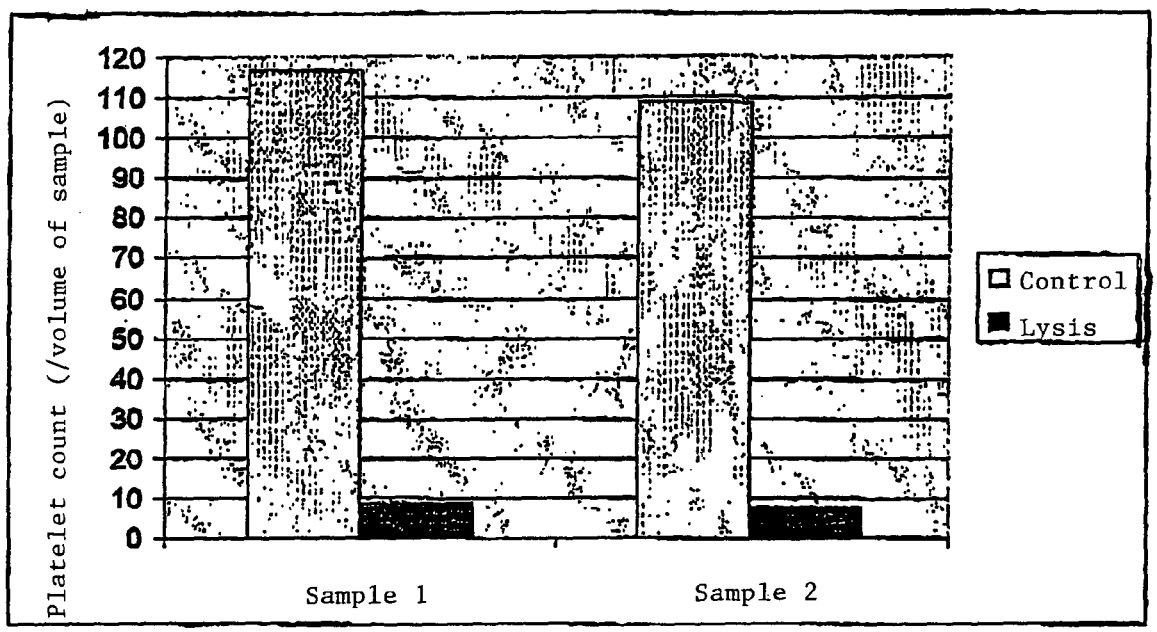
FIG. 8 is a graph showing the effect of the lysis solution on the platelet number of two platelet samples.

Reproducibility of the efficacy of the lysis solution was tested. Different platelet samples were lysed and analyzed.
Method:
one milliliter of platelets was diluted in 9 ml of lysis solution;
lysis was performed for 15 minutes at ambient temperature;
dilutions in series (1/10) were created in the PBS buffer up to $10^{-5}$;
100 µl of the sample was filtered on a CB04 membrane;
the microorganisms were labeled with an esterase substrate; and
the membrane was scanned with the analyzer.
FIG. 8 illustrates the lysis results obtained with different platelet samples.

III. Concentration of Pathogenic Microbes by Two Aggregation and Lysis Steps
Preparation of the sample by concentration of the pathogenic microbes in two steps comprised:
1) specific aggregation or agglutination of the cells of the blood product, and
2) specific lysis of the cells of the blood product.

Example 1

Specific Separation of the Platelets

Method:
A cryobead of E. coli was introduced in a tube of 9 ml of tryptone soy broth and incubated at 37° C. for 18-24 hours. The first aggregation step was performed as follows:
1 ml of platelet concentrate, 50 µl of E. coli (pure culture) and 100 µl of CD9 was mixed in the tubes;
the tubes were agitated manually for 5 minutes at ambient temperature.
The second lysis step was then performed:
900 µl of lysis buffer was added to 100 µl of filtrate after aggregation;
the mixture was maintained for 15 minutes at ambient temperature;
dilutions were performed in series: four dilutions 1/10;
100 µl of the resultant sample was filtered on a CB04 membrane;
the bacteria and platelets were labeled with an esterase substrate; and
the bacteria and platelets were counted with the analyzer.
The results obtained in performing the method for the concentration of bacteria in two steps are illustrated in Table 8 below.

TABLE 8

| Bacteria | Platelet concentrate (PC) | Aggregation agent |  | Bacteria count | % bacterial recovery |
|---|---|---|---|---|---|
| E. coli | PC |  |  | 337 |  |
| NCTC 9001 |  |  |  | 313 |  |
| E. coli | PC |  | lysis | 302 | 86% |
| NCTC 9001 |  |  |  | 256 |  |
| E. coli | PC | CD9 |  | 266 | 66% |
| NCTC 9001 |  |  |  | 161 |  |
| E. coli | PC | CD9 | lysis | 157 | 45% |
| NCTC 9001 |  |  |  | 138 |  |

Example 2

Specific Separation of the Red Cells

Method:

a cryobead of *E. coli* was introduced into a tube of 9 ml of tryptone soy broth and incubated at 37° for 18-24 hours.

The agglutination step was performed as follows:

1 ml of red cells, 50 µl of *E. coli* (pure culture) and 125 µl of lectin was mixed in the tubes;

the tubes were agitated manually for 5 minutes at ambient temperature;

filtration was performed on a filter with a porosity of 5 µm.

The second lysis step was then performed:

900 µl of lysis buffer was added to 100 µl of the filtrate after agglutination;

the mixture was maintained for 15 minutes at ambient temperature;

dilutions were performed in series: four dilutions 1/10;

100 µl of the resultant sample was filtered on a CB04 membrane;

the bacteria were labeled with an esterase substrate and of the red cells with an anti-glycophorin-PE antibody; and the bacteria and red cells were counted with the analyzer.

Table 9 below shows the results obtained with the counting of the bacteria performed after the step of agglutination of the red cells with lectin followed by the lysis step.

TABLE 9

|  |  |  |  | Bacteria counts | Bacteria recovery (%) | Red cell counts |
|---|---|---|---|---|---|---|
| E. coli NCTC 9001 | Red cells 10 |  |  | 441 449 |  | 3582 4188 |
| E. coli NCTC 9001 | Red cells 10 | lectin | lysis | 261 348 | 68 | 161 180 |

The red cell concentration was reduced by 1.5 log after agglutination. 68% of the bacteria were recovered after these two steps.

IV. Marker Agents

Example 1

Esterase substrate ChemChrome V6

Marker solutions can be prepared from an esterase substrate and used in the detection method of the invention according to the following protocol:

a) Preparation

10 µl of esterase substrate ChemChrome V6 per milliliter of ChemSol B16 buffer (500 µl of marker solution per membrane); and this solution was stored at 4° C. shielded from light for a maximum of 4 hours.

b) Use introduce a labeling buffer into a 33-mm diameter Petri dish;

distribute 500 µl of the marker solution on the buffer; and place the CB04 membrane on the filtration gradient. Filter 100 µl of the sample to be analyzed;

place the membrane on the buffer; and incubate for 15 minutes at 37° C.

Example 2

Labeled Antibody

Thus, a marker solution comprising a labeled antibody can be used according to the following protocol:

collect 90 µl of a dilution of the sample;

add 10 µl of the anti-glycophorin-PE antibody;

vortex and incubate for 15 minutes at ambient temperature shielded from the light;

add 900 µl of PBS buffer;

place the CB04 membrane in the filtration gradient;

filter under vacuum 100 µl of the solution to be analyzed; and analyze the membrane in the analyzer, reversing the primary and tertiary cables of the analyzer.

Example 3

Value of the Addition of a Bacteria Permeabilization Agent to Improve the Penetration of the Marker Method:

the strains were preserved in a tube of 9 ml of tryptone soy broth and incubated at 37° C. for 18-24 hours;

after determination of the bacteria count by esterase labeling, 3000 bacteria were inoculated in 3 mL of platelet concentrate;

the 3 mL were treated with 1 ml of the aggregation solution (CD9: clone 6B1: 30 µg/ml, Picogreen 1/2000, PEI 40 µg/mL at 80 µg/mL) for 40 minutes;

the sample was filtered through a filter with a porosity of 5 µm;

the sample was incubated in the lysis solution (chlorhexidine 5·10$^{-3}$%, NOG 0.5%, nisin 0.2 µg/ml, EDTA 5 mM) for 20 minutes;

the totality of the sample was filtered on a CB04 membrane; and counting was performed by means of a cytometer analyzer in solid phase.

V. Conclusions

The technical options for achieving the excellent conditions for the preparation of pathogenic microbes were defined by these experiments.

With regard to the platelet concentrates, these technical options comprise:

1) an aggregation step with, e.g., a platelet activator antibody such as CD9;

2) a cell lysis step with a combination of detergents such as saponin, TWEEN 20 and TRITON X 100.

With regard to the red cell concentrates:

1) an aggregation step with a lectin such as, e.g., *Phaseolus vulgaris;*

2) a cell lysis step with a combination of detergents such as saponin, TWEEN 20 and TRITON X 100.

Labeling and permeabilization of the pathogenic microbes can be performed as desired during the aggregation step, the lysis step or directly on the concentrated microbes on the last filter before analysis.

The invention claimed is:

1. A method for detecting contaminating microbes possibly present in a blood product comprising blood cells comprising:

a) providing a sterile device for concentrating microbes possibly present in a blood product containing blood cells comprising:

a first watertight, sterile tank containing a piston and at least one blood cell aggregation agent and, optionally, at least one marker agent for labeling pathogenic microbes;

a second watertight, sterile tank containing at least one lysis agent for blood cells and, optionally, at least one marker agent for labeling pathogenic microbes;

a first filter located between the first tank and the second tank, wherein the size of the pores of the first filter are between about 2 µm and about 20 µm and having pores that allow passage of contaminating microbes, but not cell aggregates;

a second filter, wherein the size of the pores of the second filter are between about 0.2 µm and about 2 µm is enclosed in a membrane support having two removable, separable parts and located downstream of the second tank and having pores that retain contaminating microbes and allow passage of cellular debris;

a first watertight, sterile connector joining the first tank and the first filter; a second watertight, sterile connector joining the first filter and the second tank; a third watertight, sterile connector joining the second tank and the second filter; a fourth watertight, sterile connector comprising a reverse lock valve and joining a bag containing a blood product to the first sterile tank, b) subjecting a sample of the blood product to an aggregation treatment of the blood cells in the first tank, c) substantially eliminating aggregates formed in step (b) by passage of the sample over the first filter to allow passage of contaminating microbes, but not cell aggregates, d) selectively lysing residual cells of the filtrate obtained in step (c) in the second tank, e) labeling the contaminating microbes with a marker agent either during step (b) or step (d), f) recovering the contaminating microbes by passage of the lysate from step (d) over the second filter to retain contaminating microbes and allow passage of cellular debris, and g) analyzing material on the second filter to detect labeled contaminating microbes possibly retained by the second filter, said method being performed in the sterile device.

2. The method according to claim 1, further comprising adding a permeabilization agent of the contaminating microbes in the first tank or second tank in at least one of the steps (b), (d) or (f).

3. The method according to claim 2, wherein the permeabilization agent is selected from the group consisting of polyethylene imine, chlorhexidine diacetate, chlorhexidine digluconate, ethylene diamine tetraacetate acid (EDTA) alone or in combination with nisin, a detergent and mixtures thereof.

4. The method according to claim 3, wherein the detergent is selected from the group consisting of N-octyl β-D-glucopyranoside, SDS, polyoxyethyleneglycol dodecyl ether and mixtures thereof.

5. The method according to claim 1, wherein the marker agent is a marker solution selected from among the group consisting of an esterase substrate, a labeled antibody and a marker of nucleic acids.

6. The method according to claim 1, wherein the marker agent comprises a fluorescent marker or an agent coupled to a fluorochrome or an enzyme enabling degradation of a substrate thereby made fluorescent.

7. The method according to claim 6, wherein fluorescence is produced using an excitation laser and detected.

8. The method according to claim 1, wherein the blood cells of the blood product are platelets or red cells or a mixture thereof.

9. The method according to claim 1, wherein the blood product comprises platelets and step (b) comprises bringing the sample into contact with an aggregation composition comprising at least one aggregation agent selected from the group consisting of 1) a specific antibody of a platelet antigen, 2) a strong agonist of platelet activation selected from the group consisting of thrombin, TRAP (thrombin receptor activating peptide), trypsin, collagen, thromboxane A2, PAF (platelet activating factor), ionophore A23187, immune complexes and complement factors, and 3) a weak agonist of platelet activation selected from the group consisting of ADP, adrenalin, arachidonic acid, Von Willebrand factor, serotonin and epinephrine.

10. The method according to claim 9, wherein concentration of the antibody is between about 0.5 µg/ml and about 50 µg/ml.

11. The method according to claim 9, wherein the antibody is selected from the group consisting of an anti-CD, anti-CD32, anti-PTA1, anti-D42, anti-GpIIb/IIIa and anti-GpIV antibody.

12. The method according to claim 1, wherein the blood product comprises red cells and step (b) comprises bringing the sample into contact with an agglutination composition comprising at least one agglutination agent selected from the group consisting of lectins, polyethylene imine, polyvinylpyrrolidone (PVP), gelatins, dextrans and polyethylene glycols (PEG).

13. The method according to claim 12, wherein the lectins have erythro agglutinin activity.

14. The method according to claim 12, wherein the lectins are selected from the group consisting of *Phaseolus vulgaris, Vicia sativa. Vicia faba* and *Erythrina corallodendron*.

15. The method according to claim 14, wherein concentration of *Phaseolus vulgaris* lectin is between about 10 µg/ml and about 200 µg/ml.

16. The method according to claim 1, wherein step (d) is performed with a lysis solution comprising one or more detergents selected from the group consisting of saponin, SDS, polyoxyethyleneglycol dodecyl ether, Polidocanol, N-octyl β-D-glucopyranoside and sodium carbonate.

17. The method according to claim 1, wherein the contaminating microbes are aerobic or anaerobic bacteria, molds, yeasts, or live and/or dead bacterial spores.

18. The method according to claim 1, wherein the size of the pores of the second filter are about 0.4 µm.

19. The method according to claim 1, wherein the contaminating microbes are aerobic or anaerobic bacteria, molds, yeasts, or live and/or dead bacterial spores, and the size of the pores of the first filter are between about 2 µm and about 20 µm, and the size of the pores of the second filter are about 0.4 µm.

20. The method according to claim 1, wherein the size of the pores of the first filter are about 11 µm or about 5 µm.

21. The method according to claim 1, wherein the contaminating microbes are aerobic or anaerobic bacteria, molds, yeasts, or live and/or dead bacterial spores, and the size of the pores of the first filter are about 11 µm or about 5 µm, and the size of the pores of the second filter are about 0.4 µm.

22. The method according to claim 1, wherein the size of the pores of the second filter are about 0.3 to less than 1 µm.

23. The method according to claim 1, wherein the contaminating microbes are aerobic or anaerobic bacteria, molds, yeasts, or live and/or dead bacterial spores, and the size of the pores of the first filter are between about 2 µm and about 20 µm, and the size of the pores of the second filter are about 0.3 to less than 1 µm.

* * * * *